(12) United States Patent
Halpern Chirch et al.

(10) Patent No.: US 10,512,601 B2
(45) Date of Patent: *Dec. 24, 2019

(54) COMPOSITIONS HAVING IMPROVED WATER RESISTANCE

(71) Applicant: L'Oréal, Paris (FR)

(72) Inventors: Susan Halpern Chirch, Basking Ridge, NJ (US); Anthony Diaz-Santana, Edison, NJ (US); Anne-Laure Suzanne Bernard, New York, NY (US)

(73) Assignee: L'Oréal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/575,419

(22) Filed: Dec. 18, 2014

(65) Prior Publication Data

US 2016/0175230 A1    Jun. 23, 2016

(51) Int. Cl.
| | | |
|---|---|---|
| A61K 8/81 | (2006.01) |
| A61Q 17/04 | (2006.01) |
| A61K 8/06 | (2006.01) |
| A61K 8/31 | (2006.01) |
| A61K 8/02 | (2006.01) |

(52) U.S. Cl.
CPC .......... *A61K 8/8152* (2013.01); *A61K 8/0241* (2013.01); *A61K 8/064* (2013.01); *A61K 8/31* (2013.01); *A61Q 17/04* (2013.01); *A61K 2800/412* (2013.01)

(58) Field of Classification Search
None
See application file for complete search history.

(56) References Cited

U.S. PATENT DOCUMENTS

| | | | |
|---|---|---|---|
| 4,804,531 A | 2/1989 | Grollier | |
| 5,616,598 A | 4/1997 | Lion et al. | |
| 5,851,517 A | 12/1998 | Mougin et al. | |
| 5,945,095 A | 8/1999 | Mougin et al. | |
| 6,235,271 B1 | 5/2001 | Luther et al. | |
| 2004/0137028 A1 | 7/2004 | de la Poterie | |
| 2005/0101740 A1* | 5/2005 | Mougin | A61K 8/90 525/242 |
| 2007/0286824 A1* | 12/2007 | Rabe | A61K 8/11 424/59 |
| 2008/0193405 A1 | 8/2008 | Mukherjee et al. | |
| 2011/0027202 A1 | 2/2011 | Candau et al. | |
| 2011/0243864 A1* | 10/2011 | Farcet | A61K 8/04 424/61 |
| 2011/0301247 A1* | 12/2011 | Hayakawa | A61K 8/891 514/772.3 |
| 2016/0317423 A1* | 11/2016 | Portal | A61K 8/044 |

FOREIGN PATENT DOCUMENTS

| | | |
|---|---|---|
| EP | 0 749 746 | 12/1996 |
| EP | 0 749 747 | 12/1996 |
| FR | 2 785 530 | 5/2000 |
| FR | 2 937 645 | 4/2010 |
| FR | 2 972 630 | 9/2012 |
| FR | 2 972 631 | 9/2012 |
| JP | H7-304644 | 11/1995 |
| JP | 10-218750 | 8/1998 |
| JP | 2008-69362 | 3/2008 |
| JP | 2013-63954 | 4/2013 |
| WO | WO 2012/072774 A1 | 6/2012 |

OTHER PUBLICATIONS

U.S. Appl. No. 14/575,636, filed Dec. 18, 2014, Halpern Chirch, et al.
International Search Report dated Apr. 18, 2016, in PCT/US2015/066665.
Written Opinion of the International Searching Authority dated Apr. 18, 2016, in PCT/US2015/066665.
Extended European Search Report dated May 15, 2018 in Patent Application No. 15871166.3, citing documents AA and AO therein, 7 pages.
Office Action dated Jul. 10, 2018, in Japanese Patent Application No. 2017-532741 (with Computer-Generated English Language Translation) citing documents AO-AQ therein, 6 pages.
U.S. Appl. No. 14/575,259, filed Dec. 18, 2014, 2016/0175204, Rita Jaky El-Khouri.
U.S. Appl. No. 14/575,866, filed Dec. 18, 2014, US2016/0175232, Rita Jaky El-Khouri.
U.S. Appl. No. 14/974,531, filed Dec. 18, 2015, 2016/0184211, Roshanak Debeaud.
U.S. Appl. No. 14/974,706, filed Dec. 18, 2015, 2016/0175205, Roshanak Debeaud.
U.S. Appl. No. 15/105,293, filed Jun. 16, 2016, 2016/0317423, Julien Portal.
U.S. Appl. No. 15/533,444, filed Jun. 6, 2017, Hong Li.
U.S. Appl. No. 15/534,216, filed Jun. 8, 2017, Roshanak Debeaud.
U.S. Appl. No. 15/537,082, filed Jun. 16, 2017, Laure Daubersies.
U.S. Appl. No. 15/537,422, Philippe Ilekti.
U.S. Appl. No. 15/537,423, Philippe Ilekti.

* cited by examiner

*Primary Examiner* — David J Blanchard
*Assistant Examiner* — Sarah J Chickos
(74) *Attorney, Agent, or Firm* — Oblon, McClelland, Maier & Neustadt, L.L.P.

(57) ABSTRACT

Compositions containing at least one sunscreen active agent and having improved water resistance properties, as well as methods of improving water resistance properties of compositions containing at least one sunscreen active agent, are provided.

17 Claims, No Drawings

COMPOSITIONS HAVING IMPROVED WATER RESISTANCE

FIELD OF THE INVENTION

The present invention relates to compositions containing at least one sunscreen active agent and having improved water resistance properties.

BACKGROUND OF THE INVENTION

Compositions containing sunscreen active agents are highly popular. Sunscreen active agents in such compositions protect keratinous material such as hair and skin from the harm caused by UV radiation, including harm from both UVA and UVB rays. A standard measure for determining the amount of protection a composition containing sunscreen active agent provides against UV radiation, particularly against UVB rays, is sun protection factor (SPF). However, one problem with compositions containing sunscreen active agent(s) is that they are often subjected to water (for example, at the beach), and if the compositions are not water resistant, the water causes the composition to be wholly or partially removed from the wearer. And, if the composition is removed from the wearer, it is unable to fully protect keratinous material from UV radiation.

Accordingly, one aspect of the present invention are compositions containing at least one sunscreen active agent and having improved water resistance properties. Another aspect of the present invention are methods of improving water resistance properties of compositions containing at least one sunscreen active agent.

SUMMARY OF THE INVENTION

The present invention relates to compositions for keratinous materials (for example, hair or skin) comprising at least one sunscreen active agent and at least one dispersion of acrylic polymer particles.

The present invention also relates to emulsion compositions for keratinous materials (for example, hair or skin) comprising at least one sunscreen active agent and at least one dispersion of acrylic polymer particles. Preferably, the composition is in the form of a water-in-oil (W/O) emulsion.

The present invention also relates to methods of increasing the water resistance properties of a composition containing at least one sunscreen active agent comprising adding at least one dispersion of acrylic polymer particles to the composition in an amount effective to increase the water resistance properties of the composition.

The present invention also relates to methods of preparing compositions having improved water resistance properties comprising adding at least one dispersion of acrylic polymer particles to the composition during preparation of the composition.

The present invention also relates to methods of making a composition comprising combining at least one sunscreen active agent and at least one dispersion of acrylic polymer particles.

It is to be understood that both the foregoing general description and the following detailed description are exemplary and explanatory only, and are not restrictive of the invention.

DETAILED DESCRIPTION OF THE INVENTION

Other than in the operating examples, or where otherwise indicated, all numbers expressing quantities of ingredients and/or reaction conditions are to be understood as being modified in all instances by the term "about."

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Volatile", as used herein, means having a flash point of less than about 100° C.

"Non-volatile", as used herein, means having a flash point of greater than about 100° C.

"Waterproof" as used herein refers to the ability to repel water and permanence with respect to water. Waterproof properties may be evaluated by any method known in the art for evaluating such properties. For example, a composition may be applied to skin, and the skin may be submerged in water for a certain amount of time. The amount of composition remaining on the skin after the pre-ascertained amount of time may then be evaluated and compared.

"Physiologically acceptable medium" is means a medium that is compatible with human keratin materials, for instance the skin, the lips, the nails, the eyelashes, the eyebrows or the hair.

"Cosmetic composition" means a composition that is compatible with keratin materials.

"Keratin materials" means the skin (body, face, contour of the eyes, scalp), head hair, eyelashes, eyebrows, bodily hairs, nails and/or lips.

Sunscreen Active Agent

According to the present invention, compositions containing at least one sunscreen active agent are provided. The sunscreen active agent(s) present in the compositions of the present invention can be organic sunscreen active agents and/or an inorganic sunscreen active agents (for example, physical blockers such as zinc oxide). Further, the sunscreen active agent(s) present in the compositions of the present invention can be soluble in water, soluble in non-aqueous material, and/or insoluble. Preferably, the sunscreen active agents are organic sunscreen active agents. Preferably, combinations of two or more sunscreens are used.

Organic sunscreens useful herein include anthranilates; cinnamic derivatives; dibenzoylmethane derivatives; salicylic derivatives; camphor derivatives; triazine derivatives, such as those disclosed in Patent Applications U.S. Pat. No. 4,367,390, EP 863 145, EP 517 104, EP 570 838, EP 796 851, EP 775 698, EP 878 469, EP 933 376, EP 507 691, EP 507 692, EP 790 243 and EP 944 624; benzophenone derivatives; β, β-diphenylacrylate derivatives; benzotriazole derivatives; benzalmalonate derivatives; benzimidazole derivatives; imidazolines; bisbenzoazolyl derivatives as disclosed in Patents EP 669 323 and U.S. Pat. No. 2,463,264; p-aminobenzoic acid (PABA) derivatives; methylenebis(hydroxyphenylbenzotriazole) derivatives as disclosed in Applications U.S. Pat. Nos. 5,237,071, 5,166,355, GB 2 303 549, DE 197 26 184 and EP 893 119; screening polymers and screening silicones, such as those disclosed in particular in Application WO 93/04665; dimers derived from α-alkylstyrene, such as those disclosed in Patent Application DE 198 55 649; 4,4-diarylbutadienes as disclosed in Applications EP 0 967 200, DE 197 46 654, DE 197 55 649, EP-A-1 008 586, EP 1 133 980 and EP 133 981; and their mixtures.

By way of illustration, mention may be made, as sunscreens which are generally active in the UV-A and/or UV-B regions, denoted below under their INCI names, of:

p-aminobenzoic acid (PABA) derivatives, in particular PABA, ethyl PABA, ethyl dihydroxypropyl PABA, ethylhexyl dimethyl PABA, glyceryl PABA or PEG-25 PABA, salicylic derivatives, in particular homosalate, ethylhexyl salicylate, dipropylene glycol salicylate, or TEA salicylate, dibenzoylmethane derivatives, in particular butyl methoxydibenzoylmethane (sold in particular under the trade name "Parsol 1789"), or isopropyl dibenzoylmethane, cinnamic derivatives, in particular ethylhexyl methoxycinnamate (sold in particular under the trade name "Parsol MCX"), isopropyl methoxycinnamate, isoamyl methoxycinnamate, cinoxate, DEA methoxycinnamate, diisopropyl methyl cinnamate, or glyceryl ethylhexanoate dimethoxycinnamate, β,β-diphenylacrylate derivatives, in particular octocrylene (sold in particular under the trade name "Uvinul N539") or etocrylene, benzophenone, in particular benzophenone-1, benzophenone-2, benzophenone-3 or oxybenzone, benzophenone-4, benzophenone-5, benzophenone-6, benzophenone-8, benzophenone-9, benzophenone-12, or n-hexyl 2-(4-diethylamino-2-hydroxybenzoyl)benzoate, benzylidene camphor derivatives, in particular 3-benzylidene camphor, 4-methylbenzylidene camphor, benzylidene camphor sulphonic acid, camphor benzalkonium methosulphate, terephthalylidene dicamphor sulphonic acid (manufactured under the name "Mexoryl SX"), or polyacrylamidomethyl benzylidene camphor (manufactured under the name "Mexoryl SW"), benzimidazole derivatives, in particular phenylbenzimidazole sulphonic acid, or disodium phenyl dibenzimidazole tetrasulphonate, triazine derivatives, in particular anisotriazine (sold under the trade name "Tinosorb S"), ethylhexyl triazone, diethylhexyl butamido triazone, or 2,4,6-tris(diisobutyl 4'-aminobenzalmalonate)-s-triazine, benzotriazole derivatives, in particular drometrizole trisiloxane or methylene bisbenzotriazolyl tetramethylbutylphenol, anthranilic derivatives, in particular menthyl anthranilate, imidazoline derivatives, in particular ethylhexyl dimethoxybenzylidene dioxoimidazoline propionate, benzalmalonate derivatives, in particular polyorganosiloxane comprising benzalmalonate functional groups, 4,4-diarylbutadiene derivatives, in particular 1,1'-dicarboxy (2,2'-dimethylpropyl)-4,4-diphenylbutadiene, and their mixtures.

Preferred organic sunscreens include ethylhexyl salicylate, ethylhexyl methoxycinnamate, octocrylene, phenylbenzimidazole sulphonic acid, benzophenone-3, benzophenone4, benzophenone-5, 4-methylbenzylidene camphor, terephthalylidene dicamphor sulphonic acid, disodium phenyl dibenzimidazole tetrasulphonate, 2,4,6-tris(diisobutyl 4'-aminobenzalmalonate)-s-triazine, anisotriazine, ethylhexyl triazone, diethylhexyl butamido triazone, methylene bisbenzotriazolyl tetramethylbutylphenol, drometrizole trisiloxane, 1,1'-dicarboxy (2,2'-dimethylpropyl)-4,4-diphenylbutadiene, and their mixtures.

Preferred inorganic sunscreens include pigments or alternatively nanopigments (mean size of the primary particles: generally between 5 nm and 100 µm, preferably between 10 nm and 50 nm) formed from coated or uncoated metal oxides, such as, for example, titanium oxide (amorphous or crystalline in the rutile and/or anatase form), iron oxide, zinc oxide, zirconium oxide or cerium oxide nanopigments. Conventional coating agents of such inorganic sunscreen active agents include alumina and/or aluminium stearate. Examples of nanopigments formed from coated or uncoated metal oxides are disclosed in particular in Patent Applications EP 518 772 and EP 518 773.

Preferred UVA absorbers generally absorb radiation in the 320 to 400 nm region of the ultraviolet spectrum. Examples of preferred UVA absorbers include anthranilates, benzophenones, and dibenzoyl methanes.

Preferred UVB absorbers generally absorb radiation in the 280 to 320 nm region of the ultraviolet spectrum. Examples of preferred UVB absorbers include camphor derivatives, cinnamates, diphenylacrylates and salicylates.

Specific examples of sunscreen active agents which absorb in the UVA and/or UVB range include:

p-aminobenzoic acid,
oxyethylene (25 mol) p-aminobenzoate,
2-ethylhexyl p-dimethylaminobenzoate,
ethyl N-oxypropylene p-aminobenzoate,
glycerol p-aminobenzoate,
4-isopropylbenzyl salicylate,
2-ethylhexyl 4-methoxycinnamate,
methyl diisopropylcinnamate,
isoamyl 4-methoxycinnamate,
diethanolamine 4-methoxycinnamate ate,
3-(4'-trimethylammunium)-benzyliden-bornan-2-one methylsulfate,
2-hydroxy-4-methoxybenzophenone,
2-hydroxy-4-methoxybenzophenone-5-sulfonate,
2,4-dihydroxybenzophenone,
2,2',4,4'-tetrahydroxybenzophenone,
2,2'-dihydroxy-4,4'dimethoxybenzophenone,
2-hydroxy-4-n-octoxybenzophenone,
2-hydroxy4-methoxy-4'-methoxybenzophenone,
(2-oxoborn-3-ylidene)-tolyl-4-sulfonic acid and soluble salts thereof,
3-(4'-sulfo)benzyliden-bornan-2-one and soluble salts thereof,
3-(4'methylbenzylidene)-d,1-camphor,
3-benzylidene-d,1-camphor,
benzene 1,4-di(3-methylidene-10-camphosulfonic) acid and salts thereof,
urocanic acid,
2,4,6-tris[p-(2'-ethylhexyl-1'-oxycarbonyl)-anilino]-1,3,5-triazine,
2-[(p-(tertiobutylamido)anilino]-4,6-bis-[(p-(2'-ethylhexyl-1'-oxycarbonyl)anilino]-1,3,5-triazine,
2,4-bis{[4-(2-ethyl-hexyloxy)]-2-hydroxy]-phenyl}-6-(4-methoxy-phenyl)-1,3,5-triazine,
the polymer of N-(2 et 4)-[(2-oxoborn-3-yliden)methyl] benzyl]-acrylamide,
1,4-bisbenzimidazolyl-phenylen-3,3',5,5'-tetrasulfonic acid and salts thereof,
the benzalmalonate-substituted polyorganosiloxanes,
the benzotriazole-substituted polyorganosiloxanes (Drometrizole Trisiloxane),
dispersed 2,2'-methylene-bis-[6-(2H-benzotriazol-2-yl)-4-(1,1,3,3-tetramethylbutyl)phenol],
solubilized 2,2'-methylene-bis-[6-(2H-benzotriazol-2-yl)-4-(methyl)phenol],
avobenzone,
2-methyldibenzoylmethane,
4-methyldibenzoylmethane,
4-isopropyldibenzoylmethane,
4-tert.-butyldibenzoylmethane,
2,4-dimethyldibenzoylmethane, 2,5-dimethyldibenzoylmethane,
4,4'-diisopropyldibenzoylmethane,
4,4'-dimethoxydibenzoylmethane,
2-methyl-5-isopropyl-4'-methoxydibenzoylmethane,
2-methyl-5-tert.-butyl-4'-methoxydibenzoylmethane,
2,4-dimethyl4'-methoxydibenzoylmethane, and
2,6-dimethyl-4-tert.-butyl-4'-methoxydibenzoylmethane.

Preferably, the sunscreen active agent(s) are present in the compositions according to the invention in amounts ranging from about 1% to about 50% by weight with respect to the total weight of the composition, preferably ranging from about 3 to about 40% by weight with respect to the total weight of the composition, preferably ranging from about 5 to about 30% by weight with respect to the total weight of the composition, including all ranges and subranges therebetween.

Dispersion of Acrylic Polymer Particles

According to the present invention, compositions containing at least one dispersion of acrylic polymer particles are provided. According to the present invention, the dispersions of acrylic polymer particles are dispersions of C1-C4 alkyl (meth)acrylate polymer particles stabilized with stabilizers based on isobornyl (meth)acrylate polymer in a hydrocarbon-based oil. The dispersion of acrylic polymer particles has been previously disclosed in PCT patent application serial no. PCT/EP2014/07800, the entire contents of which is hereby incorporated by reference.

According to preferred embodiments, the polymer of the particles is a C1-C4 alkyl (meth)acrylate polymer. The C1-C4 alkyl (meth)acrylate monomers may be chosen from methyl (meth)acrylate, ethyl (meth)acrylate, n-propyl (meth)acrylate, isopropyl (meth)acrylate, n-butyl (meth) acrylate and tert-butyl (meth)acrylate. Preferably, the monomer is a C1-C4 alkyl acrylate monomer. Preferably, the polymer of the particles is a methyl acrylate and/or ethyl acrylate polymer.

The polymer of the particles may also comprise an ethylenically unsaturated acid monomer or the anhydride thereof, chosen preferably from ethylenically unsaturated acid monomers comprising at least one carboxylic, phosphoric or sulfonic acid function, such as, for example, crotonic acid, itaconic acid, fumaric acid, maleic acid, maleic anhydride, styrenesulfonic acid, vinylbenzoic acid, vinylphosphoric acid, acrylic acid, methacrylic acid, acrylamidopropanesulfonic acid or acrylamidoglycolic acid, and/or salts thereof.

Preferably, the ethylenically unsaturated acid monomer is chosen from (meth)acrylic acid, maleic acid and maleic anhydride. The salts may preferably be chosen from salts of alkali metals, for example sodium or potassium; salts of alkaline-earth metals, for example calcium, magnesium or strontium; metal salts, for example zinc, aluminium, manganese or copper; ammonium salts of formula NH4+; quaternary ammonium salts; salts of organic amines, for instance salts of methylamine, dimethylamine, trimethylamine, triethylamine, ethylamine, 2-hydroxyethylamine, bis(2-hydroxyethyl)amine or tris(2-hydroxyethyl)amine; lysine or arginine salts.

The polymer of the particles may thus comprise or consist essentially of 80% to 100% by weight of C1-C4 alkyl (meth)acrylate and of 0 to 20% by weight of ethylenically unsaturated acid monomer, relative to the total weight of the polymer.

According to preferred embodiments, the polymer consists essentially of a polymer of one or more C1-C4 alkyl (meth)acrylate monomers.

According to preferred embodiments, the polymer consists essentially of a copolymer of C1-C4 (meth)acrylate and of (meth)acrylic acid or maleic anhydride.

The polymer of the particles may be chosen from, for example: methyl acrylate homopolymers; ethyl acrylate homopolymers; methyl acrylate/ethyl acrylate copolymers; methyl acrylate/ethyl acrylate/acrylic acid copolymers; methyl acrylate/ethyl acrylate/maleic anhydride copolymers; methyl acrylate/acrylic acid copolymers ethyl acrylate/acrylic acid copolymers; methyl acrylate/maleic anhydride copolymers; and ethyl acrylate/maleic anhydride copolymers.

Preferably, the polymer of the particles is a non-crosslinked polymer.

The polymer of the particles of the dispersion preferably has a number-average molecular weight ranging from about 2000 to about 10,000,000, preferably ranging from about 150,000 to 500,000, including all ranges and subranges therebetween.

The polymer of the particles are preferably present in the dispersion in a content ranging from about 21% to about 58.5% by weight, preferably ranging from about 36% to about 42% by weight, relative to the total weight of the dispersion, including all ranges and subranges therebetween.

The stabilizer is preferably an isobornyl (meth)acrylate polymer chosen from isobornyl (meth)acrylate homopolymer and statistical copolymers of isobornyl (meth)acrylate and of C1-C4 alkyl (meth)acrylate present in an isobornyl (meth)acrylate/C1-C4 alkyl (meth)acrylate weight ratio of greater than 4. Preferably, the weight ratio ranges from about 4.5 to about 19, including all ranges and subranges therebetween.

Preferably, the stabilizer is chosen from, for example: isobornyl acrylate homopolymers; statistical copolymers of isobornyl acrylate/methyl acrylate; statistical copolymers of isobornyl acrylate/methyl acrylate/ethyl acrylate; statistical copolymers of isobornyl methacrylate/methyl acrylate, in the weight ratio described previously.

The stabilizing polymer preferably has a number-average molecular weight ranging from about 10,000 to about 400,000, preferably ranging from about 20,000 to about 200,000, including all ranges and subranges therebetween.

Although not wishing to be bound by any particular theory, it is believed that the stabilizer is in contact with the surface of the polymer particles and thus makes it possible to stabilize these particles at the surface in order to keep these particles in dispersion in the non-aqueous medium of the dispersion.

Preferably, the combination of the stabilizer+polymer of the particles present in the dispersion comprises from about 10% to about 50% by weight of polymerized isobornyl (meth)acrylate, and from about 50% to about 90% by weight of polymerized C1-C4 alkyl (meth)acrylate, relative to the total weight of the combination of the stabilizer+polymer of the particles.

Preferably, the combination of the stabilizer+polymer of the particles present in the dispersion comprises from about 15% to about 30% by weight of polymerized isobornyl (meth)acrylate, and from about 70% to about 85% by weight of polymerized C1-C4 alkyl (meth)acrylate, relative to the total weight of the combination of the stabilizer+polymer of the particles.

The oily medium of the polymer dispersion comprises a hydrocarbon-based oil.

The hydrocarbon-based oil is an oil that is liquid at room temperature (25° C.).

The term "hydrocarbon-based oil" means an oil formed essentially from, or even consisting of, carbon and hydrogen atoms, and optionally oxygen and nitrogen atoms, and not containing any silicon or fluorine atoms. It may contain, for example, alcohol, ester, ether, carboxylic acid, amine and/or amide groups.

The hydrocarbon-based oil may be chosen from, for example:
- hydrocarbon-based oils containing from 8 to 14 carbon atoms, preferably:
  - branched C8-C14 alkanes, for instance C8-C14 isoalkanes of petroleum origin (also known as isoparaffins), for instance isododecane (also known as 2,2,4,4,6-pentamethylheptane), isodecane and, for example, the oils sold under the trade name Isopar or Permethyl,
  - linear alkanes, for instance n-dodecane (C12) and n-tetradecane (C14) sold by Sasol under the respective references Parafol 12-97 and Parafol 14-97, and also mixtures thereof, the undecane-tridecane mixture, the mixtures of n-undecane (C11) and of n-tridecane (C13) obtained in Examples 1 and 2 of patent application WO 2008/155 059 from the company Cognis, the disclosure of which is hereby incorporated by reference, and mixtures thereof,
  - short-chain esters (containing from 3 to 8 carbon atoms in total) such as ethyl acetate, methyl acetate, propyl acetate or n-butyl acetate,
- hydrocarbon-based oils of plant origin such as triglycerides consisting of fatty acid esters of glycerol, the fatty acids of which may have chain lengths varying from C4 to C24, these chains possibly being linear or branched, and saturated or unsaturated; these oils are especially heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion-flower oil and musk rose oil; shea butter; or else caprylic/capric acid triglycerides, for instance those sold by the company Stéarineries Dubois or those sold under the names Miglyol 810®, 812® and 818® by the company Dynamit Nobel,
- synthetic ethers containing from 10 to 40 carbon atoms;
- linear or branched hydrocarbons of mineral or synthetic origin, such as petroleum jelly, polydecenes, hydrogenated polyisobutene such as Parleam®, squalane and liquid paraffins, and mixtures thereof,
- synthetic esters such as oils of formula R1COOR2 in which R1 represents a linear or branched fatty acid residue containing from 1 to 40 carbon atoms and R2 represents an, in particular, branched hydrocarbon-based chain containing from 1 to 40 carbon atoms, on condition that R1+R2≥10, for instance purcellin oil (cetostearyl octanoate), isopropyl myristate, isopropyl palmitate, C12 to C15 alkyl benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, alkyl or polyalkyl heptanoates, octanoates, decanoates or ricinoleates such as propylene glycol dioctanoate; hydroxylated esters such as isostearyl lactate, diisostearyl malate and 2-octyldodecyl lactate; polyol esters and pentaerythritol esters,
- fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol.

Preferably, the hydrocarbon-based oil is apolar (formed solely from carbon and hydrogen atoms).

The hydrocarbon-based oil is preferably chosen from hydrocarbon-based oils containing from 8 to 14 carbon atoms, in particular the apolar oils described previously. Preferably, the hydrocarbon-based oil is isododecane.

The polymer particles of the dispersion preferably have an average size, especially a number-average size, ranging from about 50 to about 500 nm, preferably ranging from about 75 to about 400 nm, and preferably ranging from about 100 to about 250 nm, including all ranges and subranges therebetween.

In general, the dispersion according to the invention may be prepared in the following manner, which is given as an example.

The polymerization may be performed in dispersion, i.e. by precipitation of the polymer during formation, with protection of the formed particles with a stabilizer. In a first step, the stabilizing polymer is prepared by mixing the constituent monomer(s) of the stabilizing polymer, with a radical initiator, in a solvent known as the synthesis solvent, and by polymerizing these monomers. In a second step, the constituent monomer(s) of the polymer of the particles are added to the stabilizing polymer formed and polymerization of these added monomers is performed in the presence of the radical initiator.

When the non-aqueous medium is a non-volatile hydrocarbon-based oil, the polymerization may be performed in an apolar organic solvent (synthesis solvent), followed by adding the non-volatile hydrocarbon-based oil (which should be miscible with the said synthesis solvent) and selectively distilling off the synthesis solvent. A synthesis solvent which is such that the monomers of the stabilizing polymer and the free-radical initiator are soluble therein, and the polymer particles obtained are insoluble therein, so that they precipitate therein during their formation, is thus chosen. In particular, the synthesis solvent may be chosen from alkanes such as heptane or cyclohexane.

When the non-aqueous medium is a volatile hydrocarbon-based oil, the polymerization may be performed directly in the oil, which thus also acts as synthesis solvent. The monomers should also be soluble therein, as should the free-radical initiator, and the polymer of the particles obtained should be insoluble therein.

The monomers are preferably present in the synthesis solvent, before polymerization, in a proportion of about 5 to about 20% by weight. The total amount of monomers may be present in the solvent before the start of the reaction, or part of the monomers may be added gradually as the polymerization reaction proceeds. The free-radical initiator is preferably azobisisobutyronitrile or tert-butyl peroxy-2-ethylhexanoate.

The polymerization may be performed at a temperature ranging from about 70 to about 110° C.

The polymer particles are surface-stabilized, when they are formed during the polymerization, by means of the stabilizer.

The stabilization may be performed by any known means, and in particular by direct addition of the stabilizer, during the polymerization. The stabilizer is preferably also present in the mixture before polymerization of the monomers of the polymer of the particles. However, it is also possible to add it continuously, especially when the monomers of the polymer of the particles are also added continuously.

From about 10% to about 30% by weight, preferably from about 15% to about 25% by weight of stabilizer may be used, relative to the total weight of monomers used (stabilizer+polymer of the particles).

The polymer particle dispersion preferably comprises from about 30% to about 65% by weight, preferably from about 40% to about 60% by weight of solids, relative to the total weight of the dispersion.

Preferably, the oily dispersion may comprise a plasticizer, for example, a plasticizer chosen from tri-n-butyl citrate, tripropylene glycol monomethyl ether (INCI name: PPG-3 methyl ether) and trimethyl pentaphenyl trisiloxane (sold under the name Dow Corning PH-1555 HRI Cosmetic Fluid by the company Dow Corning). These plasticizers make it possible to improve the mechanical strength of the polymer film. The plasticizer, if present, may be present in the oily dispersion in an amount ranging from about 5% to about 50% by weight, relative to the total weight of the polymer of the particles.

According to preferred embodiments, the polymer of the particles is a C1-C4 alkyl (meth)acrylate polymer; the stabilizer is an isobornyl (meth)acrylate polymer chosen from isobornyl (meth)acrylate homopolymer and statistical copolymers of isobornyl (meth)acrylate and of C1-C4 alkyl (meth)acrylate present in an isobornyl (meth)acrylate/C1-C4 alkyl (meth)acrylate weight ratio of greater than 4. For these statistical stabilizing copolymers, the defined weight ratio makes it possible to obtain a polymer dispersion that is stable, especially after storage for seven days at room temperature (25° C.).

The dispersions according to the invention consist of particles, which are generally spherical, of at least one surface-stabilized polymer, in a non-aqueous medium.

Preferably, the amount of acrylic polymer particles present in the compositions of the present invention ranges from about 5 to about 50% by weight based on total weight of the composition, preferably about 7% to about 40% by weight based on the total weight of the composition, preferably about 10% to about 25% by weight based on the total weight of the composition, including all ranges and subranges therebetween.

Preferably, the acrylic polymer particles are present in an amount effective to increase the water resistance of the composition by at least 25%, preferably by at least 30%, preferably by at least 35%, including all ranges and subranges therebetween such as, for example, 25% to 100%, 25% to 75%, 25% to 50%, 25% to 40%, and all ranges and subranges therebetween.

Preferably, the acrylic polymer particles and sunscreen active agent(s) are present in the compositions and methods of the invention in a weight ratio between 3:1 and 1:3, preferably between 2:1 and 1:2, and preferably between 1.5:1 and 1:1.5. Preferably, more sunscreen active agent(s) are present than acrylic polymer particles on a weight basis.

Water

The compositions of the present invention may also contain water. When the compositions of the present invention contain water, they are preferably in the form of an emulsion. Preferably, when the compositions of the present invention contain water, they are in the form of an water-in-oil emulsion (W/O). When present, water is preferably present in an amount of from about 5% to about 50% by weight, preferably from about 10% to about 40% by weight, preferably from about 20% to about 40% by weight, including all ranges and subranges therebetween, all weights being based on the total weight of the composition.

Optional Ingredients

The compositions of the present invention may also include any one, or more, optional ingredients. Examples thereof include, but are not limited to, co-solvents (volatile and/or non-volatile), surfactants, plasticizers, preservatives, fillers, active ingredients, colorants (pigments and/or dyes), waxes, thickening agents, film forming agents and SPF boosters.

The compositions according to the invention are preferably intended for topical application to keratinous material such as the skin and/or hair. Accordingly, the compositions of the present invention preferably contain a physiologically acceptable medium. Of course, the components of the physiologically acceptable medium of the present invention will depend upon the intended use of the composition as one of ordinary skill in the art would understand that different cosmetic compositions generally contain ingredients useful for the specific type of composition (for example, a shampoo could contain ingredients such as surfactants, a conditioner could contain ingredients such as emollients and/or humectants, a moisturizer could contain ingredients such as emollients, moisturizers and/or active agents, and a sunscreen composition could contain ingredients such as preservatives, film forming agents and SPF boosters, among other things).

Needless to say, the composition of the invention should be cosmetically or dermatologically acceptable, i.e., it should contain a non-toxic physiologically acceptable medium and should be able to be applied to the skin, superficial body growths or the lips of human beings.

According to preferred embodiments of the present invention, methods of increasing the water resistance properties of a composition containing at least one sunscreen active agent comprising adding at least one dispersion of acrylic polymer particles to the composition in an amount effective to increase the water resistance properties of the composition are provided. In accordance with these methods, the amount of acrylic polymer particles added to the composition preferably ranges from about 5 to about 50% by weight based on total weight of the composition, preferably about 7% to about 40% by weight based on the total weight of the composition, preferably about 10% to about 25% by weight based on the total weight of the composition, including all ranges and subranges therebetween. Preferably, the acrylic polymer particles are sufficiently effective to increase the water resistance by at least 25%, preferably by at least 30%, preferably by at least 35%, including all ranges and subranges therebetween such as, for example, 25% to 100%, 25% to 75%, 25% to 50%, 25% to 40%, and all ranges and subranges therebetween.

According to preferred embodiments, methods of preparing compositions having improved water resistance properties comprising adding at least one dispersion of acrylic polymer particles to the composition during preparation of the composition are provided. In accordance with these methods, the amount of acrylic polymer particles added to the composition preferably ranges from about 5 to about 50% by weight based on total weight of the composition, preferably about 7% to about 40% by weight based on the total weight of the composition, preferably about 10% to about 25% by weight based on the total weight of the composition, including all ranges and subranges therebetween. Preferably, the acrylic polymer particles are sufficiently effective to increase the water resistance by at least 25%, preferably by at least 30%, preferably by at least 35%, including all ranges and subranges therebetween such as, for example, 25% to 100%, 25% to 75%, 25% to 50%, 25% to 40%, and all ranges and subranges therebetween.

According to yet other preferred embodiments, methods of making a composition comprising combining at least one sunscreen active agent and at least one dispersion of acrylic polymer particles during preparation are provided.

The compositions and methods of the present invention can "comprise," "consist of" or "consist essentially of" the identified ingredients and process steps. For purposes of the compositions and methods of the present invention where the invention "consists essentially of" the identified ingredients and/or process steps, the sole "basic and novel property" of such compositions and/or methods is water resistance. Further, given that it is contemplated that other water resistance enhancers (for example, film forming agents) can be added to the invention methods and compositions in the context of the present invention, a "material effect" on the basic and novel property of the invention can only be an adverse effect. That is, because positive effects on water resistance (such as those effected by film forming agents) are within the scope of the present invention, only ingredients which have a material adverse effect on water resistance would be relevant to determining whether or not compositions or methods "consist essentially of" the required elements.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

Example 1

In a first step, 1300 g of isododecane, 337 g of isobornyl acrylate, 28 g of methyl acrylate and 3.64 g of tert-butyl peroxy-2-ethylhexanoate (Trigonox 21 S from Akzo) were placed in a reactor. The isobornyl acrylate/methyl acrylate mass ratio is 92/8. The mixture was heated at 90° C. under argon with stirring.

After 2 hours of reaction, 1430 g of isododecane were added to the reactor feedstock and the mixture was heated to 90° C.

In a second step, a mixture of 1376 g of methyl acrylate, 1376 g of isododecane and 13.75 g of Trigonox 21S were run in over 2 hours 30 minutes, and the mixture was left to react for 7 hours. 3.3 litres of isododecane were then added and part of the isododecane was evaporated off to obtain a solids content of 50% by weight.

A dispersion of methyl acrylate particles stabilized with a statistical copolymer stabilizer containing 92% isobornyl acrylate and 8% methyl acrylate in isododecane was obtained.

The oily dispersion contains in total (stabilizer+particles) 80% methyl acrylate and 20% isobornyl acrylate.

The polymer particles of the dispersion have a number-average size of about 160 nm. The dispersion is stable after storage for 7 days at room temperature (25° C.).

Example 2

A dispersion of polymer in isododecane was prepared according to the preparation method of Example 1, using:

Step 1: 275.5 g of isobornyl acrylate, 11.6 g of methyl acrylate, 11.6 g of ethyl acrylate, 2.99 g of Trigonox 21, 750 g of isododecane; followed by addition, after reaction, of 750 g of isododecane.

Step 2: 539.5 g of methyl acrylate, 539.5 g of ethyl acrylate, 10.8 g of Trigonox 21S, 1079 g of isododecane. After reaction, addition of 2 litres of isododecane and evaporation to obtain a solids content of 35% by weight.

A dispersion in isododecane of methyl acrylate/ethyl acrylate (50/50) copolymer particles stabilized with an isobornyl acrylate/methyl acrylate/ethyl acrylate (92/4/4) statistical copolymer stabilizer was obtained.

The oily dispersion contains in total (stabilizer+particles) 40% methyl acrylate, 40% ethyl acrylate and 20% isobornyl acrylate.

The dispersion is stable after storage for 7 days at room temperature (25° C.).

Example 3

A dispersion of polymer in isododecane was prepared according to the preparation method of Example 1, using:

Step 1: 315.2 g of isobornyl acrylate, 12.5 g of methyl acrylate, 12.5 g of ethyl acrylate, 3.4 g of Trigonox 21, 540 g of isododecane, 360 g of ethyl acetate; followed by addition, after reaction, of 540 g of isododecane and 360 g of ethyl acetate.

Step 2: 303 g of methyl acrylate, 776 g of ethyl acrylate, 157 g of acrylic acid, 11 g of Trigonox 21S, 741.6 g of isododecane and 494.4 g of ethyl acetate. After reaction, addition of 3 litres of an isododecane/ethyl acetate mixture (60/40 weight/weight) and total evaporation of the ethyl acetate and partial evaporation of the isododecane to obtain a solids content of 44% by weight.

A dispersion in isododecane of methyl acrylate/ethyl acrylate/acrylic acid (24.5/62.8/12.7) copolymer particles stabilized with an isobornyl acrylate/methyl acrylate/ethyl acrylate (92/4/4) statistical copolymer stabilizer was obtained.

The oily dispersion contains in total (stabilizer+particles) 10% acrylic acid, 20% methyl acrylate, 50% ethyl acrylate and 20% isobornyl acrylate.

The dispersion is stable after storage for 7 days at room temperature (25° C.).

Example 4

A dispersion of polymer in isododecane was prepared according to the preparation method of Example 1, using:

Step 1: 315.2 g of isobornyl acrylate, 12.5 g of methyl acrylate, 12.5 g of ethyl acrylate, 3.4 g of Trigonox 21, 540 g of isododecane, 360 g of ethyl acetate; followed by addition, after reaction, of 540 g of isododecane and 360 g of ethyl acetate.

Step 2: 145 g of methyl acrylate, 934 g of ethyl acrylate, 157 g of acrylic acid, 12.36 g of Trigonox 21S, 741.6 g of isododecane and 494.4 g of ethyl acetate. After reaction, addition of 3 litres of an isododecane/ethyl acetate mixture (60/40 weight/weight) and total evaporation of the ethyl acetate and partial evaporation of the isododecane to obtain a solids content of 44% by weight.

A dispersion in isododecane of methyl acrylate/ethyl acrylate/acrylic acid (11.7/75.6/12.7) copolymer particles stabilized with an isobornyl acrylate/methyl acrylate/ethyl acrylate (92/4/4) statistical copolymer stabilizer was obtained.

The oily dispersion contains in total (stabilizer+particles) 10% acrylic acid, 10% methyl acrylate, 60% ethyl acrylate and 20% isobornyl acrylate.

The dispersion is stable after storage for 7 days at room temperature (25° C.).

Example 5

A dispersion of polymer in isododecane was prepared according to the preparation method of Example 1, using:

Step 1: 48 g of isobornyl acrylate, 2 g of methyl acrylate, 2 g of ethyl acrylate, 0.52 g of Trigonox 21, 57.6 g of isododecane, 38.4 g of ethyl acetate; followed by addition, after reaction, of 540 g of isododecane and 360 g of ethyl acetate.

Step 2: 98 g of methyl acrylate, 73 g of ethyl acrylate, 25 g of maleic anhydride, 1.96 g of Trigonox 21S, 50.4 g of isododecane and 33.60 g of ethyl acetate. After reaction, addition of 1 litre of an isododecane/ethyl acetate mixture (60/40 weight/weight) and total evaporation of the ethyl acetate and partial evaporation of the isododecane to obtain a solids content of 46.2% by weight.

A dispersion in isododecane of methyl acrylate/ethyl acrylate/maleic anhydride (50/37.2/12.8) copolymer particles stabilized with an isobornyl acrylate/methyl acrylate/ethyl acrylate (92/4/4) statistical copolymer stabilizer was obtained.

The oily dispersion contains in total (stabilizer+particles) 10% maleic anhydride, 30% methyl acrylate, 40% ethyl acrylate and 20% isobornyl acrylate.

The dispersion is stable after storage for 7 days at room temperature (25° C.).

Example 6

A dispersion of polymer in isododecane was prepared according to the preparation method of Example 1, using:

Step 1: 48.5 g of isobornyl methacrylate, 4 g of methyl acrylate, 0.52 g Trigonox 21, 115 g of isododecane; followed by addition, after reaction, of 80 g of isododecane.

Step 2: 190 g of methyl acrylate, 1.9 g of Trigonox 21S, 190 g of isododecane. After reaction, addition of 1 litre of isododecane and partial evaporation of the isododecane to obtain a solids content of 48% by weight.

A dispersion in isododecane of methyl acrylate polymer particles stabilized with an isobornyl methacrylate/methyl acrylate (92/8) statistical copolymer stabilizer was obtained.

The oily dispersion contains in total (stabilizer+particles) 80% methyl acrylate and 20% isobornyl methacrylate.

The dispersion is stable after storage for 7 days at room temperature (25° C.).

Examples 7 and 8

Several oily dispersions of polymethyl acrylate stabilized with a stabilizer containing isobornyl acrylate and optionally methyl acrylate were prepared, according to the procedure of Example 1, by varying the mass ratio of isobornyl acrylate and methyl acrylate and observing the stability of the dispersion obtained as a function of the chemical constitution of the stabilizer.

All the dispersions comprise in total (stabilizer+particles) 80% methyl acrylate and 20% isobornyl acrylate.

Example 7

Step 1: 50 g of isobornyl acrylate, 0.5 g Trigonox 21, 96 g of isododecane; followed by addition, after reaction, of 80 g of isododecane.

Step 2: 200 g of methyl acrylate, 2 g of Trigonox 21S, 200 g of isododecane. After reaction, addition of 80 g of isododecane and evaporation to obtain a solids content of 31% by weight.

A dispersion in isododecane of polymethyl acrylate particles stabilized with a polyisobornyl acrylate stabilizer was obtained.

Example 8

Step 1: 48.5 g of isobornyl acrylate, 8.5 g of methyl acrylate, 0.57 g Trigonox 21, 115 g of isododecane; followed by addition, after reaction, of 75 g of isododecane.

Step 2: 185.5 g of methyl acrylate, 1.85 g of Trigonox 21S, 185.5 g of isododecane. After reaction, addition of 75 g of isododecane and evaporation to obtain a solids content of 31% by weight.

A dispersion in isododecane of polymethyl acrylate particles stabilized with an isobornyl acrylate/methyl acrylate (85/15) statistical copolymer stabilizer was obtained.

Example 9 (Invention)

The following water-in-oil emulsion composition of the present invention was prepared:

| Phase | Chemical Name | % wt/wt |
|---|---|---|
| A | Isododecane | 4.74 |
|   | Oil Dispersion of Example 3 | 21.46 |
|   | Isononyl Isononanoate | 5.00 |
|   | Capryl Methicone | 5.00 |
|   | Dimethicone (2 cSt) | 10.00 |
|   | Polyglyceryl-4 Isostearate | 0.51 |
|   | Cetyl PEG/PPG-10/1 Dimethicone | 1.49 |
|   | Organic Sunscreen Active Agents | 20.00 |
| B | Water | 30.00 |
|   | Disodium EDTA | 0.20 |
|   | Phenoxyethanol | 0.20 |
|   | Propylene Glycol | 0.70 |
|   | Chlorphenesin | 0.20 |
|   | Sodium Chloride | 0.50 |

The emulsion composition was prepared by mixing the ingredients of phase A together and heating it to 75 to 80° C., mixing the ingredients of phase B together and heating it to 75 to 80° C., and adding phase B to phase A slowly while homogenizing using a Silverson homogenizer at 7000-8000 rpm for 15 minutes at 75 to 80° C., and then cooled.

Example 10 (Comparative)

The following comparative water-in-oil emulsion composition of the present invention was prepared via the same methodology as in Example 9:

| Phase | Chemical Name | % wt/wt |
|---|---|---|
| A | Isododecane | 26.20 |
| | Isononyl Isononanoate | 5.00 |
| | Capryl Methicone | 5.00 |
| | dimethicone (2 cSt) | 10.00 |
| | Polyglyceryl-4 Isostearate | 0.51 |
| | Cetyl PEG/PPG-10/1 Dimethicone | 1.49 |
| | Organic Sunscreen Active Agents | 20.00 |
| B | Water | 30.00 |
| | Disodium EDTA | 0.20 |
| | Phenoxyethanol | 0.20 |
| | Propylene Glycol | 0.70 |
| | Chlorphenesin | 0.20 |
| | Sodium Chloride | 0.50 |

The water-resistance of the compositions of Examples 13 and 14 were determined via the following methodology:

Sample Preparation
1. 32.5 mg (1.3 mg/cm$^2$) of sunscreen product was applied on the ROUGH side of a clean plate (N=3).
2. The sample was allowed to dry and settle for 15 minutes at room temperature.
3. The in vitro SPF value was determined using Lab-Sphere (5 measurements per plate).

Apparatus Procedure
1. Bath was set to 25° C., paddle RPM to 25RPM, and immersion time to 20 min.
2. Plates were allowed to dry at room temperature for 30 minutes.
3. The in vitro SPF was determined again using Lab-Sphere (5 measurements per plate).

Water-resistance was determined as follows based on the preceding measurements.

Mathematical definition of in vitro water resistance $$\text{in vitro } WR = \frac{SPF_f}{SPF_i} \times 100$$

$SPF_i$ = SPF initial $SPF_f$ = SPF post 20 minute immersion

The following results were obtained.

| | Example 9 (invention) | Example 10 (comparative) |
|---|---|---|
| Avg | 89.23 | 63.80 |
| Std. Dev. | 1.17 | 5.95 |

Then, the increase in water-resistance provided by the dispersion of acrylic polymer particles was calculated by the following formula to be an increase of 39.86%:

Mathematical definition of percent increase:

$$\text{Increase \%} = \frac{(WR_{InEx} - WR_{CompEx})}{WR_{CompEx}} \times 100$$

What is claimed is:

1. A composition comprising:
(a) from 3% to 40%, by weight with respect to the total weight of the composition, of one or more organic sunscreen active agent(s); and
(b) at least one dispersion of acrylic polymer particles, wherein the at least one dispersion of acrylic polymer particles consists of particles of a C1-C4 alkyl (meth)acrylate polymer and at least one stabilizer selected from the group consisting of isobornyl (meth)acrylate homopolymers and statistical copolymers of isobornyl (meth)acrylate and of C1-C4 alkyl (meth)acrylate present in an isobornyl (meth)acrylate/C1-C4 alkyl (meth)acrylate weight ratio of greater than 4,
wherein the at least one dispersion of acrylic polymer particles consisting of particles of a C1-C4 alkyl (meth)acrylate polymer and at least one stabilizer selected from the group consisting of isobornyl (meth)acrylate homopolymers and statistical copolymers of isobornyl (meth)acrylate and of C1-C4 alkyl (meth)acrylate present in an isobornyl (meth)acrylate/C1-C4 alkyl (meth)acrylate weight ratio of greater than 4 is present in an amount effective to increase water resistance of the composition.

2. The composition of claim 1, wherein the composition is an emulsion.

3. The composition of claim 2, wherein the emulsion is a water-in-oil emulsion.

4. The composition of claim 1, wherein the composition consists essentially of said one or more organic sunscreen active agent(s) and said at least one dispersion of acrylic polymer particles wherein the at least one dispersion of acrylic polymer particles consists of particles of a C1-C4 alkyl (meth)acrylate polymer and at least one stabilizer selected from the group consisting of isobornyl (meth)acrylate homopolymers and statistical copolymers of isobornyl (meth)acrylate and of C1-C4 alkyl (meth)acrylate present in an isobornyl (meth)acrylate/C1-C4 alkyl (meth)acrylate weight ratio of greater than 4.

5. The composition of claim 4, further comprising at least one film forming agent.

6. The composition of claim 1, wherein the composition comprising, by weight, more of the organic sunscreen active agent(s) than the C1-C4 alkyl (meth)acrylate polymer particles.

7. The composition of claim 1, wherein the at least one dispersion of acrylic polymer particles consisting of particles of a C1-C4 alkyl (meth)acrylate polymer and at least one stabilizer selected from the group consisting of isobornyl (meth)acrylate homopolymers and statistical copolymers of isobornyl (meth)acrylate and of C1-C4 alkyl (meth)acrylate present in an isobornyl (meth)acrylate/C1-C4 alkyl (meth)acrylate weight ratio of greater than 4 is present in an amount effective to increase water resistance of the composition between 25% and 50%.

8. The composition of claim 1, wherein the C1-C4 alkyl (meth)acrylate polymer of the acrylic polymer particles is a methyl acrylate and/or ethyl acrylate polymer.

9. The composition of claim 1, wherein the C1-C4 alkyl (meth)acrylate polymer of the acrylic polymer particles is at least one selected from the group consisting of:
methyl acrylate homopolymers;
ethyl acrylate homopolymers;
methyl acrylate/ethyl acrylate copolymers;
methyl acrylate/ethyl acrylate/acrylic acid copolymers;
methyl acrylate/ethyl acrylate/maleic anhydride copolymers;
methyl acrylate/acrylic acid copolymers;
ethyl acrylate/acrylic acid copolymers;
methyl acrylate/maleic anhydride copolymers; and
ethyl acrylate/maleic anhydride copolymers.

10. The composition of claim 1, wherein the C1-C4 alkyl (meth)acrylate polymer particles have an average size ranging from 75 nm to 400 nm.

11. The composition of claim 1, wherein the at least one stabilizer is at least one selected from the group consisting of:
- isobornyl acrylate homopolymers;
- statistical copolymers of isobornyl acrylate/methyl acrylate;
- statistical copolymers of isobornyl acrylate/methyl acrylate/ethyl acrylate; and
- statistical copolymers of isobornyl methacrylate/methyl acrylate.

12. The composition of claim 1, further comprising at least one hydrocarbon oil containing from 8 to 14 carbon atoms.

13. The composition of claim 12, wherein the at least one hydrocarbon oil is isododecane.

14. The composition of claim 1, wherein the composition comprises from 5% to 30%, by weight with respect to the total weight of the composition, of one or more organic sunscreen active agent(s).

15. The composition of claim 1, wherein the C1-C4 alkyl (meth)acrylate polymer particles have an average size ranging from 100 nm to 250 nm.

16. The composition of claim 1, wherein the at least one stabilizer is at least one selected from the group consisting of:
- statistical copolymers of isobornyl acrylate/methyl acrylate;
- statistical copolymers of isobornyl acrylate/methyl acrylate/ethyl acrylate; and
- statistical copolymers of isobornyl methacrylate/methyl acrylate.

17. The composition of claim 1, wherein the at least one dispersion of acrylic polymer particles consisting of particles of a C1-C4 alkyl (meth)acrylate polymer and at least one stabilizer selected from the group consisting of isobornyl (meth)acrylate homopolymers and statistical copolymers of isobornyl (meth)acrylate and of C1-C4 alkyl (meth)acrylate present in an isobornyl (meth)acrylate/C1-C4 alkyl (meth)acrylate weight ratio of greater than 4 is present in an amount effective to increase water resistance of the composition by at least 25%.

* * * * *